United States Patent
Hu et al.

(10) Patent No.: US 8,373,003 B2
(45) Date of Patent: Feb. 12, 2013

(54) METHOD OF REMOVING HEAVY HYDROCARBONS FROM REACTION PRODUCTS IN THE PRODUCTION OF SEC-BUTYL ACETATE

(75) Inventors: Xiannian Hu, Yueyang (CN); Hua Li, Yueyang (CN); Pingxiang Xi, Yueyang (CN)

(73) Assignee: Hunan Zhongchuang Chemical Co., Ltd., Yueyang, Hunan Province (CN)

( * ) Notice: Subject to any disclaimer, the term of this patent is extended or adjusted under 35 U.S.C. 154(b) by 421 days.

(21) Appl. No.: 12/675,576

(22) PCT Filed: Jun. 25, 2008

(86) PCT No.: PCT/CN2008/071434
§ 371 (c)(1),
(2), (4) Date: Feb. 26, 2010

(87) PCT Pub. No.: WO2009/033381
PCT Pub. Date: Mar. 19, 2009

(65) Prior Publication Data
US 2010/0305355 A1    Dec. 2, 2010

(30) Foreign Application Priority Data

Sep. 14, 2007 (CN) .......................... 2007 1 0035741
Nov. 30, 2007 (CN) .......................... 2007 1 0192466

(51) Int. Cl.
*C07C 67/00* (2006.01)
(52) U.S. Cl. ...................................... 560/241
(58) Field of Classification Search .......... None
See application file for complete search history.

(56) References Cited

U.S. PATENT DOCUMENTS
5,599,976 A * 2/1997 Scates et al. ............ 562/519

FOREIGN PATENT DOCUMENTS
CN    101007761    *    8/2007
JP    58183640         10/1983
JP    5163201           6/1993

OTHER PUBLICATIONS
Derwent Abstract of CN 101007761.*

* cited by examiner

*Primary Examiner* — Karl J Puttlitz
(74) *Attorney, Agent, or Firm* — Volpe and Koenig, P.C.

(57) ABSTRACT

The present invention relates to a method of removing heavy hydrocarbon from reaction products in producing sec-butyl acetate, characterized in that the method comprises: drawing out materials from the enrichment area of the heavy hydrocarbon; contacting the materials with water sufficiently to make the heavy hydrocarbon in materials and the water stratify naturally wherein the heavy hydrocarbon is contained in the upper layer and the water is contained in the lower layer; and discharging the upper layer and recycling the lower layer into the system. The enrichment area of heavy hydrocarbon refers to the area enriched with heavy hydrocarbon and formed in the bottom of an azeotropic distillation tower during the process of azeotropic separation, while the process of azeotropic separation refers to a process of feeding the mixture of sec-butyl acetate, acetate acid and heavy hydrocarbon into the azeotropic distillation tower and adding azeotropic agent into the azeotropic distillation tower to conduct azeotropic distillation, then evaporating the azeotropic mixture formed by sec-butyl acetate and azeotropic agent from the top of the azeotropic distillation tower, and meanwhile, the acetic acid and the heavy hydrocarbon falling into the bottom of the tower.

9 Claims, 2 Drawing Sheets

METHOD OF REMOVING HEAVY HYDROCARBONS FROM REACTION PRODUCTS IN THE PRODUCTION OF SEC-BUTYL ACETATE

FIELD OF THE INVENTION

The present invention relates to a process of separating products in organic chemical reactions, and more particularly, the invention relates to a process of separating the products from the reaction of producing sec-butyl acetate with acetic acid and butene or mixed C4.

BACKGROUND OF THE INVENTION

Sec-butyl acetate is also called as secondary butyl acetate, which is one of the four isomers of butyl acetate. Sec-butyl acetate is an inflammable, colorless liquid with fruity odor, and the property of the sec-butyl acetate is similar to other isomers in most situations. Various resins and organic compounds can be dissolved into the sec-butyl acetate. The boiling point of the sec-butyl acetate is lower than those of n-butyl ester and isobutyl ester which are commonly used, and the evaporation rate of the sec-butyl acetate is faster. Therefore, it is mainly used as a solvent, reaction medium, extracting agent composition, metal cleaning agent, and fruit perfume, and it is also used in medical and pharmaceutical industry.

Compared with traditional processes of producing sec-butyl acetate, the process of using 1-butene and 2-butene as raw materials to react with acetic acid has advantages of wide raw material sources, good economic benefits and being environment-friendly. Therefore, lots of researchers pay close attention to the above synthesis process, nevertheless, the research on separation and purification process of the above reaction is less reported.

A method for producing sec-butyl acetate is disclosed in U.S. Pat. No. 5,457,228, which uses acetic acid to react with 1-butene and 2-butene, and has a relatively high olefin conversion ratio and products selectivity. With regard to the separation process, it refers that the sec-butyl acetate can be separated from the reaction mixture with distillation, but no concrete separation process is disclosed. Accordingly, the purity of the products after separation isn't disclosed, either.

The inventors of the present application have disclosed a method of separating sec-butyl acetate from the reaction mixtures of the reaction between acetic acid and butene or mixed C4 in Chinese Patent Application No. CN 200710200148X, which comprises the steps of (1) feeding the reaction mixture produced in the reaction of acetic acid and mixed C4 into a flash tower, and removing the remaining mixed C4 and light component from the top of the flash tower by flash evaporation; (2) feeding the reaction products from the bottom of the flash tower into an azeotropic distillation tower, adding an azeotropic agent A, and separating sec-butyl acetate from acetic acid by azeotropic distillation; (3) feeding the materials from the top of the azeotropic distillation tower into a purification tower, and obtaining the sec-butyl acetate by distillation; (4) when the amount of the azeotropic agent A contained in acetic acid obtained from the lower part of the azeotropic distillation tower has effects on carrying out the reaction, catalytic activity, or catalyst lifetime, feeding the materials from the lower part of the azeotropic distillation tower into an acid concentrating tower, adding azeotropic agent B, then concentrating the acetic acid by another azeotropic distillation and recycling the concentrated acetic acid, or when the amount of the azeotropic agent A contained in acetic acid obtained from the lower part of the azeotropic distillation tower has no effects on carrying out the reaction, catalytic activity, and catalyst lifetime, recycling the materials from the lower part of the azeotropic distillation tower directly to the reaction system.

In the above process of producing sec-butyl acetate with raw materials of acetic acid and butene or mixed C4, it does not mention that in raw materials the butene or mixed C4 will polymerize to form heavy hydrocarbon. In addition, it does not refer to the methods of separating and removing acetic acid, sec-butyl acetate and heavy hydrocarbon from reaction mixtures.

SUMMARY OF THE INVENTION

In order to solve the above problems in the prior art, the present invention provides a method of removing heavy hydrocarbon from reaction products in producing sec-butyl acetate, which has the advantages of low energy consumption, low material consumption, high heavy hydrocarbon removal performance, and high separation efficiency, and can improve operational condition and the quality of products.

In order to solve the above technique problems, an object of the present invention is to provide a method of removing heavy hydrocarbons from reaction products in producing sec-butyl acetate, characterized in that it comprises: drawing out materials from an enrichment area of heavy hydrocarbon; making the materials contact with water sufficiently to make the heavy hydrocarbon in materials and the water stratify naturally wherein the heavy hydrocarbon is contained in the upper layer and the water is contained in the lower layer; and discharging the upper layer, and recycling the lower layer into the system.

The heavy hydrocarbon in present invention refers to polymerized products of C4 in raw materials. The method provided in the present invention can remove heavy hydrocarbon having 8 or more carbon atoms, and more particularly, the method can easily remove heavy hydrocarbon having 10 or more carbon atoms. The enrichment area of heavy hydrocarbon in present invention refers to the area which has the higher relative concentration of heavy hydrocarbon in mixed materials. In the enrichment area, the content of heavy hydrocarbon is more than 1% by mass, and more particularly, it refers to the area where the content of heavy hydrocarbon is more than 5% by mass. After separating the remaining unreacted mixed C4 and the light component and using azeotropic agent to separate the sec-butyl acetate and acetic acid, the area formed in the bottom of the azeotropic distillation tower is the enrichment area of heavy hydrocarbon mentioned in the present invention. Concretely speaking, the azeotropic separation process of sec-butyl acetate and acetic acid refers to the process of feeding the mixture of sec-butyl acetate, acetate acid and heavy hydrocarbon into the azeotropic distillation tower, adding an azeotropic agent to conduct azeotropic distillation, then evaporating the azeotropic mixture formed by sec-butyl acetate and the azeotropic agent from the top of the azeotropic distillation tower, and meanwhile, the acetic acid and the heavy hydrocarbon falling into the bottom of the tower. The azeotropic agent refers to any substance that can form an azeotropic mixture with sec-butyl acetate, and the difference between the azeotropic point of the azeotropic mixture and the boiling point of the acetic acid is 10 or more.

In the above technical solution, the materials drawn out from the enrichment area of the heavy hydrocarbon may refer to the remaining materials after drawing out the acetic acids from the lateral line in the lower part of the azeotropic distillation tower. The materials drawn out from the enrichment area of the heavy hydrocarbon mainly contain heavy hydrocarbon, acetic acid, and a little amount of sec-butyl acetate and water. If the heavy hydrocarbon is not removed from the bottom of the azeotropic distillation tower in time, it will accumulate in the bottom of the tower. When the amount of the accumulated heavy hydrocarbon becomes more, it will scale in the reboiler in the bottom of the azeotropic distillation tower, which will influence the effect of heat transfer, deteriorate the separation effect, increase energy consumption, make operation more difficult, and threaten the normal running of the whole device. Therefore, it is necessary to deal with the materials in the bottom of the azeotropic distillation tower. As the acetic acid is miscible with water, the sec-butyl acetate is soluble in water slightly, the heavy hydrocarbon is hardly soluble in water, and the densities of heavy hydrocarbon and sec-butyl acetate are lower than that of water, so when the materials drawn out from the enrichment area of heavy hydrocarbon are contacted with water sufficiently, the materials and the water will stratify naturally, that is, the heavy hydrocarbon is contained in the upper layer, and the water is contained in the lower layer. The upper layer is discharged and the lower layer is recycled into the system. Because the sec-butyl acetate will be discharged from the system together with heavy hydrocarbon, which will increase the material consumption, the content of sec-butyl acetate in drawn out materials should be reduced as much as possible. Meanwhile, the azeotropic mixture formed by sec-butyl acetate and water is distilled from the top of the azeotropic distillation tower in the process of azeotropic distillation, thus the amount of sec-butyl acetate in the bottom of the azeotropic distillation tower is relatively less.

During the contacting of the materials drawn out from the enrichment area of the heavy hydrocarbon with water, the flow ratio by mass of water to the materials is in the range of 0 to 20, preferably 0 to 10. If the flow ratio by mass of water to the materials is larger than 20, the consumption is too much more. When the flow ratio by mass of water to material is 0, materials are fed through the standing water layer.

A heavy hydrocarbon washing device used for contacting materials with water sufficiently may be any device that can be used for transferring materials, such as a water washing can, water washing tower or water washing tank etc. In the heavy hydrocarbon washing device, the water contains acetic acid after contacting with the materials in the bottom of the tower, and it can be recycled into the azeotropic distillation tower at any part of the azeotropic distillation tower, preferably the feeding port. In a special condition that the flow ratio by mass of water to materials is 0, the materials in the bottom of the tower are fed through the standing water layer, and it is necessary to timely detect the content of the acetic acid in heavy hydrocarbon separated from the top of the heavy hydrocarbon washing device. When the acid content in the heavy hydrocarbon is more than 1%, it illustrates that the acid concentration in the water is too high, and the acetic acid in the materials in the bottom of the tower can not be dissolved completely, which causes part of the acetic acid to be dissolved in the heavy hydrocarbon and discharged together with the heavy hydrocarbon. At that time, the water in the heavy hydrocarbon washing device should be recycled into the azeotropic distillation tower, and then additional water should be supplemented into the heavy hydrocarbon washing device.

In the above technical solutions, the mixture of sec-butyl acetate, acetic acid and heavy hydrocarbon to be separated is mainly produced in the process of producing sec-butyl acetate using acetic acid and butene or mixed C4. If using the catalyst distillation process in the reaction, it will obtain reaction mixture of sec-butyl acetate, remaining unreacted acetic acid, and heavy hydrocarbon; if using the tubular fixed-bed process, it will obtain the reaction mixture of sec-butyl acetate, remaining unreacted acetic acid, remaining unreacted butene or mixed C4, light components, and heavy hydrocarbon. Because the boiling points of butene or mixed C4 and light components are far lower than those of sec-butyl acetate, acetic acid, and heavy hydrocarbon, it is possible to remove the remaining butene or the mixed C4 and the light components in the mixture by flash distillation. Therefore, in any one of above processes of producing sec-butyl acetate, the products to be separated in the present invention all mainly include sec-butyl acetate, acetic acid and heavy hydrocarbon. In the above technical solutions, the separation process of heavy hydrocarbon in the mixed products has been described. Furthermore, the azeotropic separation of sec-butyl acetate and acetic acid before separating heavy hydrocarbon will be described as follows.

Because the boiling point of sec-butyl acetate is close to that of acetic acid, it is suitable to separate sec-butyl acetate and acetic acid by azeotropic distillation. In the present invention, an azeotropic agent is selected to separate sec-butyl acetate from acetic acid completely, for the reasons that it can form an azeotropic mixture with sec-butyl acetate, and the difference of boiling point between the azeotropic mixture and the acetic acid is large. In the present invention, preferred azeotropic agent is water. The azeotropic agent is added according to the composition of azeotropic mixture formed by sec-butyl acetate and azeotropic agent. When water is used as an azeotropic agent, the water is added into the azeotropic distillation tower according to the ratio of sec-butyl acetate to water which is 4 to 1 (weight percent).

In the above process of azeotropic distillation, the temperature in the bottom of the azeotropic distillation tower is controlled in the range of 100 to 130, preferably 105 to 125. If the temperature is higher than 130, the acetic acid will enter the top of the tower, while if the temperature is lower than 100, the azeotropic mixture formed by sec-butyl acetate and azeotropic agent will not be distilled to the top of the tower efficiently. The temperature in the top of the azeotropic distillation tower is controlled in the range of 75 to 100, preferably 78 to 90. The sec-butyl acetate and the azeotropic agent are distilled from the top of azeotropic distillation tower, and after cooling down, the sec-butyl acetate and the azeotropic agent are stratified naturally. The azeotropic agent or both of the azeotropic agent and the sec-butyl acetate, as refluxing component, refluxes to the top of the azeotropic distillation tower, and the sec-butyl acetate entraining a little amount of azeotropic agent can be further depurated. The acetic acid, the heavy hydrocarbon and a little amount of the sec-butyl acetate drop into the bottom of azeotropic distillation tower. Part of acetic acid may be drawn out from the lateral line in the lower part of azeotropic distillation tower and recycled to the reaction system of producing sec-butyl acetate, and the remaining materials are fed into the water washing device to carry out the above separation process of heavy hydrocarbon.

Compared with the prior art, in the process of producing sec-butyl acetate with acetic acid and butene or mixed C4, the advantages of methods in present invention are as follows: the effective separation of the mixed products can be realized, in which the sec-butyl acetate and the acetate in the mixed products are separated effectively, and in the meantime the impurities such as the heavy hydrocarbon are also separated from the system. Furthermore, the separation process not only relieves the state of scaling in the reboiler in the bottom of the azeotropic distillation tower effectively, and ensures the whole device normal running for a long time, but also improves the products quality and operational condition, and cuts down the energy consumption and material consumption.

DETAILED DESCRIPTION OF THE INVENTION

Hereinafter, the present invention will be described in way of examples by referring to the accompanying drawings, but the present invention is not limited to the examples.

EXAMPLE 1

Figure 1:
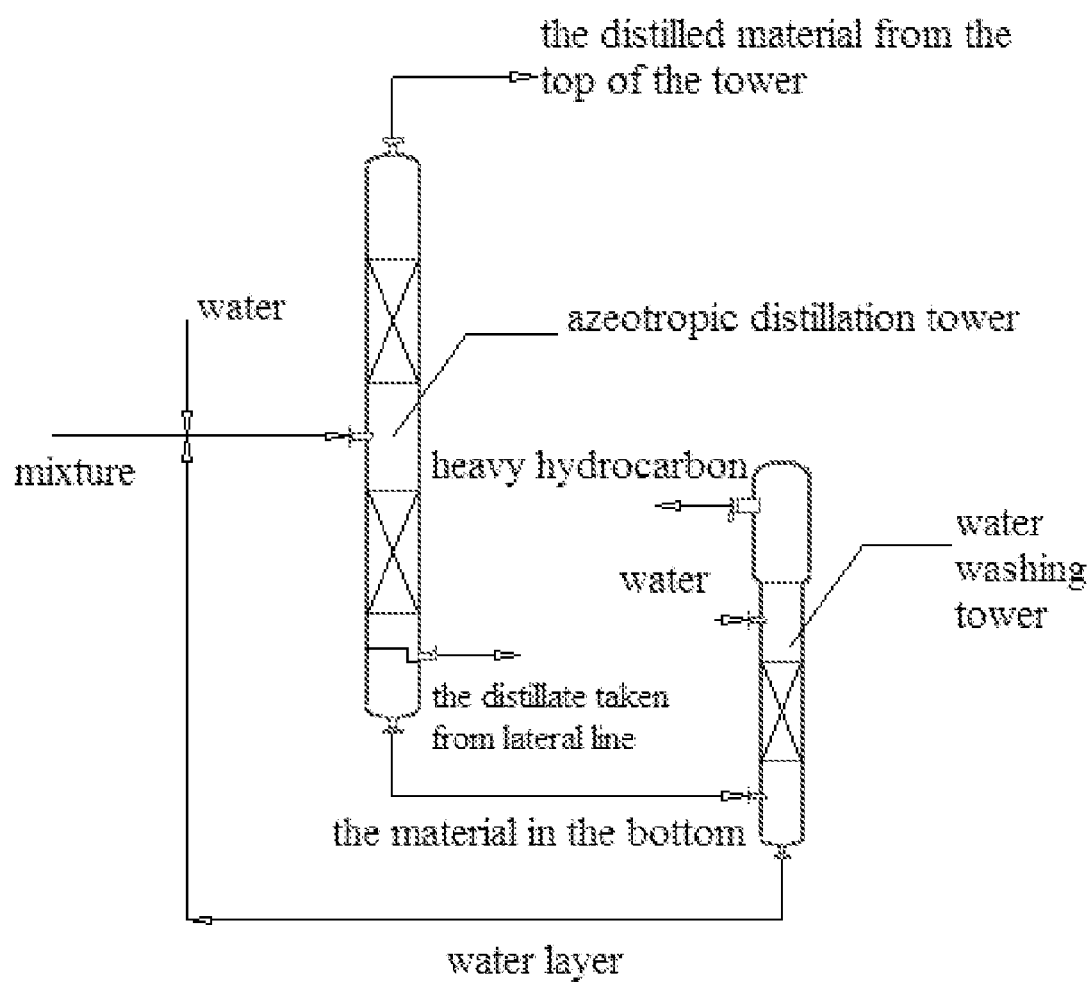
FIG. 1 illustrates the products separation process of the examples in present invention.

In the process of producing sec-butyl acetate, the remaining mixed C4 and the light component were removed from the mixture of the reaction products, and then the mixture of the reaction products was mixed with water which was used as an azeotropic agent to separate the acetic acid from the sec-butyl acetate. The enrichment area of the heavy hydrocarbon was at the bottom of the azeotropic distillation tower. As shown in FIG. 1, the materials were drawn out from the bottom of the azeotropic distillation tower and fed into the lower part of the water washing tower with the mass flow of 100 Kg/hr. The water was inpoured into the upper part of the water washing tower with the mass flow of 800 Kg/hr (the mass flow ratio of the water to the materials was 8). After the water was contacted with the materials reversely, the heavy hydrocarbon was removed from the upper layer of the water washing tower (i.e., the top of the water washing tower), and the water was drawn out from the bottom of the water washing tower, and then the water was inpoured into the system (i.e., the azeotropic distillation tower) again.

The heavy hydrocarbon which were obtained from the reaction and accumulated in the system can be taken out in time after the above operations, accordingly, the content of the heavy hydrocarbon in the bottom of the azeotropic distillation tower can be controlled in the range of 1% to 5% by mass. Furthermore, the phenomenon of scaling was decreased in reboiler on the bottom of the azeotropic distillation tower. After the device was continuously operated for one month, no obvious phenomenon of the scaling existed in the bottom of the azeotropic distillation tower.

EXAMPLE 2

The same process as Example 1 was performed, except that the mass flow of the materials in the lower part of water washing tower was changed to 100 Kg/hr, and the mass flow of water inpoured into the upper part of the water washing tower was changed to 150 Kg/hr (the mass flow ratio of water to materials was 1.5). The content of the heavy hydrocarbon in the bottom of the azeotropic distillation tower can be controlled in the range of 1% to 5% by mass after the above operations, and after the device was continuously operated for six months, no obvious phenomenon of scaling existed in reboiler on the bottom of the azeotropic distillation tower.

COMPARATIVE EXAMPLE

The process was carried out in the similar manner as in Example 2, except that the materials in the bottom of the azeotropic distillation tower were not drawn out and washed with water. As a result, the content of the heavy hydrocarbon in the bottom of the azeotropic distillation tower increased gradually and the mass content of the heavy hydrocarbon in the materials in the bottom of the azeotropic distillation tower reached up to about 30% after one month. In addition, the phenomenon of scaling was very obvious and serious in reboiler on the bottom of the azeotropic distillation tower. The direct influence of the scaling in the reboiler was that: the heat transfer of the reboiler became worse, and the azeotropic mixture formed by sec-butyl acetate and water could not be distilled into the top of the tower, which led to the worse separation effect.

EXAMPLE 3

Figure 2:
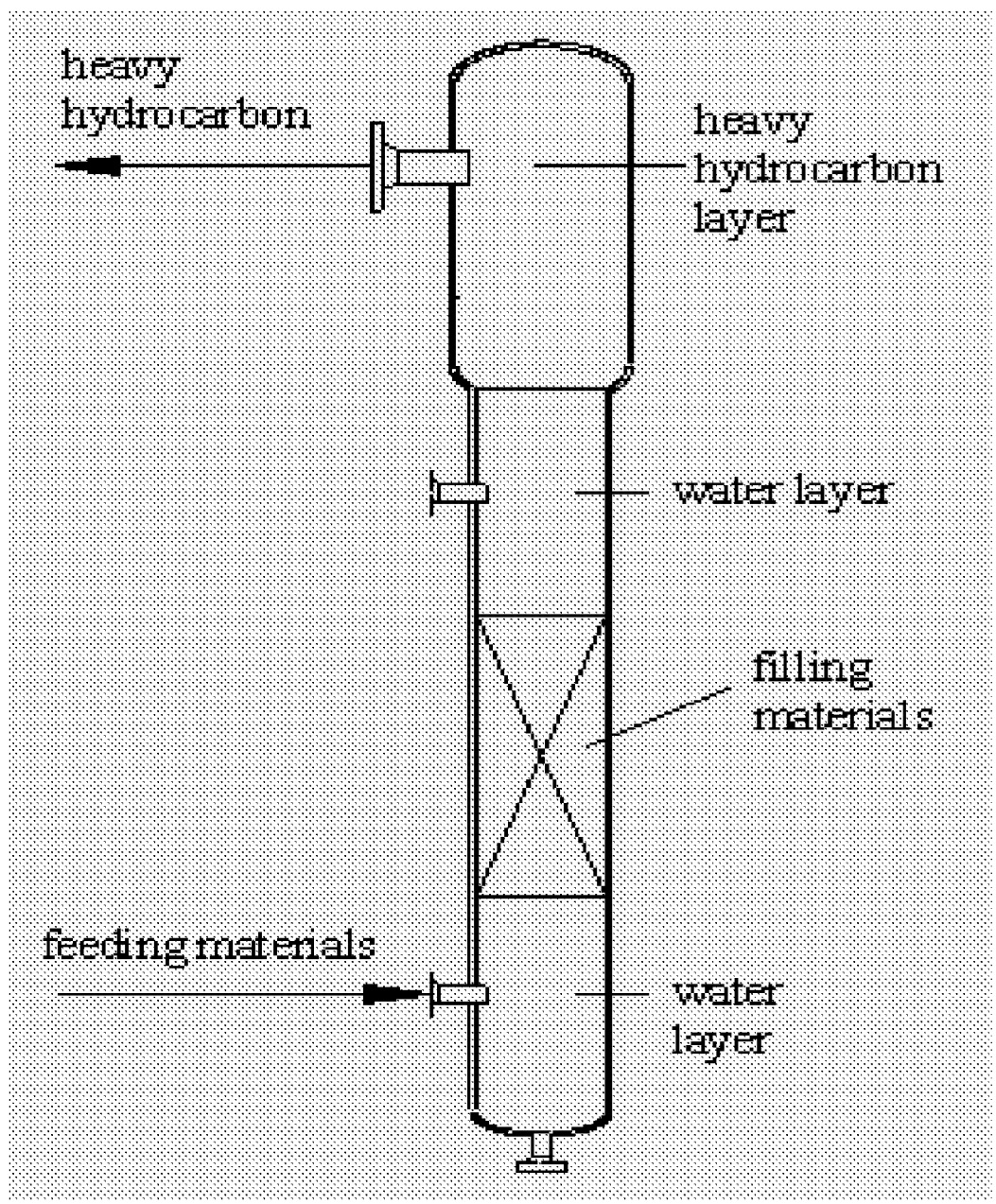
FIG. 2 illustrates the water washing tower used in example 3.

In the process of producing the sec-butyl acetate, the remaining mixed C4 and the light component were removed from the reaction mixture, and then the reaction mixture were mixed with water which was used as an azeotropic agent to separate the acetic acid from the sec-butyl acetate, and the bottom of the azeotropic distillation tower became the enrichment area of the heavy hydrocarbon. As shown in FIG. 2, the materials in the bottom of the azeotropic distillation tower were drawn out and fed into the lower part of the water washing tower filled with water and the mass flow of materials was 100 Kg/hr. The water in the water washing tower was standing, that is, the mass flow ratio of the water to the materials was 0. When the materials were fed into the tower, the water was fully contacted with the materials and then the heavy hydrocarbon was removed from the upper part of the water washing tower. When the amount of the acids in the heavy hydrocarbons was higher than 0.5%, the water in the water washing tower was inpoured into the system and also additional water was supplied into the water washing tower in the meantime.

The heavy hydrocarbon obtained in reaction and accumulated in the system can be taken out in time after the above operations, and the content of the heavy hydrocarbon in the bottom of the azeotropic distillation tower can be controlled in the range of 1% to 5% by mass, and the phenomenon of scaling in the reboiler in the bottom of the azeotropic distillation tower was decreased. After the device was continuously operated for 80 days, no obvious phenomenon of scaling existed in reboiler on the bottom of the azeotropic distillation tower.

EXAMPLE 4

In FIG. 1, the mixture consisting of sec-butyl acetate 52.28%, acetic acid 43.22%, and hydrocarbon and other materials 4.5% (mass percentage) were fed into the azeotropic distillation tower, and then, the water as the azeotropic agent was added into the azeotropic distillation tower, wherein the mass ratio of the sec-butyl acetate to the water is 4 to 1. The temperature in the bottom of the azeotropic distillation tower was 120, and the temperature in the top of the tower was 85.5. The distilled materials obtained from the top of the tower after the azeotropic distillation consisted of sec-butyl acetate 94.613%, acetic acid 0.007%, water 0.98%, hydrocarbon and other materials 4.4% (mass percentage). The distilled materials can be further refined.

The distillates taken from lateral line in the lower part of the azeotropic distillation tower consisted of sec-butyl acetate 7.28%, acetic acid 89.3%, water 0.42%, hydrocarbon and other materials 3% (mass percentage). The distillates taken from the lateral line were recycled to the reaction system.

The materials in the bottom of the azeotropic distillation tower were fed into the lower part of the water washing tower, and the mass flow of the materials in the bottom of the tower was 100 Kg/hr, and then the water was inpoured into the upper part of the water washing tower, and the mass flow of the water was 800 Kg/hr (the mass flow ratio of the water to the materials was 8). After the water was contacted with the materials reversely, the heavy hydrocarbon was removed from the top of the water washing tower, the water was drawn out from the lower of the tower and was inpoured into the feed inlet of the azeotropic distillation tower again. The heavy hydrocarbon obtained in reaction and accumulated in the system can be taken out in time after the water washing process, and the content of the heavy hydrocarbon in the bottom of the azeotropic distillation tower was controlled in the range of 1% to 5% by mass. After the device was operated continuously for one month, no obvious phenomenon of scaling existed in reboiler on the bottom of the azeotropic distillation tower.

COMPARATIVE EXAMPLE

The reaction mixture and the azeotropic distillation condition were the same as those in example 1 except that the materials were not drawn out from the bottom of the azeotropic distillation tower and washed with water. As a result, the content of the heavy hydrocarbon in the bottom of the azeotropic distillation tower increased gradually, and after one month, the content of the heavy hydrocarbon in the bottom of the azeotropic distillation tower was up to about 30% by mass. In addition, the phenomenon of scaling was very obvious and serious in the reboiler in the bottom of the azeotropic distillation tower. The direct influence of the scaling in the reboiler was that: the heat transfer of the reboiler got worse and the azeotropic mixture formed by sec-butyl acetate and water could not be distilled into the top of the tower, which led to worse separation effect and higher energy consumption.

EXAMPLE 5

The mixture consisting of sec-butyl acetate 56.26%, acetic acid 40.24%, hydrocarbon and other materials 3.5% (mass percentage) were fed into the azeotropic distillation tower, and then the water as the azeotropic agent was added into the azeotropic distillation tower, the mass ratio of sec-butyl acetate to water is 4 to 1. The temperature in the bottom of the azeotropic distillation tower was 105, and the temperature in the tower top was 78.1. The distilled materials from the top of the tower consisted of sec-butyl acetate 95.99%, acetic acid 0.01%, water 0.9%, hydrocarbon and other materials 3.1%, and the distilled materials can be further refined.

The distillates taken from lateral line in the lower part of the azeotropic distillation tower consisted of sec-butyl acetate 8.32%, acetic acid 88.17%, water 0.51%, hydrocarbon and other materials 3% (mass percentage). The distillates taken from lateral line in the lower part were recycled to the reaction system.

The materials drawn out from the bottom of the azeotropic distillation tower were fed into the lower part of the water washing tower and the mass flow of materials in the bottom of the tower was 100 Kg/hr. Then the water was inpoured into the upper part of the water washing tower and the mass flow of water was 500 Kg/hr (the mass flow ratio of the water to the materials was 5). Other steps were the same as example 1. The heavy hydrocarbon obtained in reaction and accumulated in the system can be taken out in time after the water washing operation, and the content of the heavy hydrocarbon in the bottom of the azeotropic distillation tower was controlled in the range of 1% to 5% by mass. After the device was operated continuously for six months, no obvious phenomenon of scaling existed in reboiler on the bottom of the azeotropic distillation tower.

EXAMPLE 6

The mixture consisting of sec-butyl acetate 52.79%, acetic acid 42.71%, hydrocarbon and other materials 4.5% (mass percentage) were fed into the azeotropic distillation tower, and then the water as the azeotropic agent was inpoured into the azeotropic distillation tower with the mass ratio of sec-butyl acetate to water being 4:1. The temperature in the bottom of the azeotropic distillation tower was 128, and the temperature in the top of the tower was 86.5. The distilled materials from the top of the tower after the azeotropic distillation consisted of (by mass) sec-butyl acetate 95.94%, acetic acid 0.01%, water 1%, hydrocarbon and other materials 3.05%. The distilled materials can be further refined.

The distillates taken from lateral line in the lower part of the azeotropic distillation tower consisted of sec-butyl acetate 13.68%, acetic acid 77.61%, water 4.5%, hydrocarbon and other materials 4.21% (mass percentage). The distillates taken from lateral line were recycled to the reaction system.

The materials drawn out from the bottom of the azeotropic distillation tower were fed into the lower part of the water washing tower and the mass flow of materials in the bottom of the azeotropic distillation tower was 100 Kg/hr. Then the water was inpoured into the upper part of the water washing tower and the mass flow of the water was 1000 Kg/hr (the mass flow ratio of the water to the materials was 10). Other steps were carried out in the same as in example 1. The heavy hydrocarbon obtained in reaction and accumulated in the system can be taken out in time after the water washing operation, and the content of heavy hydrocarbons in the bottom of the azeotropic distillation tower was controlled in the range of 1% to 5% by mass. After the device was operated continuously for 20 days, no obvious phenomenon of scaling existed in the reboiler in the bottom of the azeotropic distillation tower.

EXAMPLE 7

The mixture consisting of sec-butyl acetate 52.53%, acetic acid 42.75%, hydrocarbons and other materials 4.72% (mass percentage) were fed into the azeotropic distillation tower, then the water as azeotropic agent was inpoured into the azeotropic distillation tower in the mass ratio of sec-butyl acetate to water with 4 to 1. The temperature in the bottom of the azeotropic distillation tower was 125, and the temperature in the tower top was 89.5. The distilled materials from the top of the tower after the azeotropic distillation consisted of sec-butyl acetate 95.09%, acetic acid 0.01%, water 0.9%, hydrocarbons and other materials 4% (mass percentage). The distilled materials can be further refined.

The distillates taken from lateral line in the lower part of the azeotropic distillation tower consisted of sec-butyl acetate 14.7%, acetic acid 80.2%, water 0.9%, hydrocarbon and other materials 4.2% (mass percentage). The distillates taken from lateral line were recycled to the reaction system.

The materials in the bottom of the azeotropic distillation tower were fed into the lower part of the water washing tower and the mass flow of the materials in the bottom of azeotropic distillation tower was 100 Kg/hr. The water in the water washing tower was standing, that is, the mass flow ratio of the water to materials is 0. When the acid content in the heavy hydrocarbon was more than 1%, the water in the water washing tower was inpoured into the azeotropic distillation tower, and also additional water was supplied into the water washing tower in the meantime. Other steps were carried out the same as example 1. The heavy hydrocarbon obtained in reaction and accumulated in the system can be taken out in time after the water washing operation, and the content of the heavy hydrocarbon in the bottom of the azeotropic distillation tower was controlled in the range of 1% to 5% by mass. After the device was operated continuously for 80 days, no obvious phenomenon of scaling existed in the reboiler in the bottom of the azeotropic distillation tower.

What is claimed is:

1. A method of removing heavy hydrocarbon from reaction products containing sec-butyl acetate, acetic acid and heavy hydrocarbon in a reaction system producing sec-butyl acetate, wherein the heavy hydrocarbon refers to the hydrocarbon having 8 or more carbon atoms, comprising:

feeding the reaction products into an azeotropic distillation tower and adding an azeotropic agent into the azeotropic distillation tower, conducting azeotropic distillation, and then drawing out materials from an enrichment area of heavy hydrocarbon formed in the bottom of the azeotropic distillation tower; contacting the materials with water sufficiently to make the heavy hydrocarbon in the materials and the water stratify naturally into stratified substances, wherein the heavy hydrocarbon is contained in an upper layer of the stratified substances and the water is contained in a lower layer of the stratified substances; and discharging the upper layer and recycling the lower layer into the azeotropic distillation tower.

2. The method according to claim 1, wherein the flow ratio by mass of the water to the materials is in the range of 0 to 20 during the step of contacting the materials with water.

3. The method according to claim 2, wherein the flow ratio by mass of the water to the materials is in the range of 0 to 10 during the step of contacting the materials with water.

4. The method according to claim 1, wherein in the step of conducting azeotropic distillation, an azeotropic mixture formed by sec-butyl acetate, and the azeotropic agent is evaporated from the top of the azeotropic distillation tower while acetic acid and the heavy hydrocarbon fall into the bottom of the tower;

said materials refer to substances remaining after the acetic acid is drawn out from a lateral line in the lower part of the azeotropic distillation tower;

said azeotropic agent refers to any substance that is capable of forming the azeotropic mixture with the sec-butyl acetate, and the difference between the azeotropic point of the mixture and the boiling point of the acetic acid is 10° C. or more.

5. The method according to claim 4, wherein said azeotropic agent is water.

6. The method according to claim 5, wherein the temperature in the bottom of the azeotropic distillation tower is controlled in a range of 100° C. to 130°C., and the temperature in the top of the azeotropic distillation tower is controlled in a range of 75° C. to 100° C.

7. The method according to claim 6, wherein the temperature in the bottom of the azeotropic distillation tower is controlled in a range of 105° C. to 125°C., and the temperature in the top of the azeotropic distillation tower is controlled in a range of 78° C. to 90° C.

8. The method according to claim 7, wherein said acetic acid which is drawn out from the lateral line in the lower part of the azeotropic distillation tower is recycled to the reaction system producing the sec-butyl acetate.

9. The method according to claim 4, wherein said acetic acid which is drawn out from the lateral line in the lower part of the azeotropic distillation tower is recycled to the reaction system producing the sec-butyl acetate.

* * * * *